(12) United States Patent
Li et al.

(10) Patent No.: US 8,974,785 B2
(45) Date of Patent: Mar. 10, 2015

(54) FULLY HUMANIZED ANTI-HER2 ANTIBODY, PREPARATION METHOD AND USE THEREOF

(75) Inventors: Chuan Li, Shanghai (CN); Xin Tong, Shanghai (CN); Ying Kan, Shanghai (CN)

(73) Assignee: Shanghai Biomabs Pharmaceuticals Co., Ltd., Shanghai (CN)

( * ) Notice: Subject to any disclaimer, the term of this patent is extended or adjusted under 35 U.S.C. 154(b) by 310 days.

(21) Appl. No.: 13/579,180

(22) PCT Filed: Apr. 16, 2010

(86) PCT No.: PCT/CN2010/000511
§ 371 (c)(1),
(2), (4) Date: Aug. 15, 2012

(87) PCT Pub. No.: WO2011/103700
PCT Pub. Date: Sep. 1, 2011

(65) Prior Publication Data
US 2012/0309942 A1    Dec. 6, 2012

(30) Foreign Application Priority Data
Feb. 25, 2010    (CN) .......................... 2010 1 0125241

(51) Int. Cl.
| | |
|---|---|
| *C07K 16/00* | (2006.01) |
| *C07K 16/32* | (2006.01) |
| *C07K 16/30* | (2006.01) |
| *A61K 39/00* | (2006.01) |

(52) U.S. Cl.
CPC ............. *C07K 16/32* (2013.01); *C07K 16/3015* (2013.01); *A61K 2039/505* (2013.01); *C07K 2317/56* (2013.01); *C07K 2317/21* (2013.01); *C07K 2317/622* (2013.01); *C07K 2317/73* (2013.01)
USPC .................. 424/133.1; 536/23.53; 435/320.1; 530/387.3

(58) Field of Classification Search
None
See application file for complete search history.

(56) References Cited

FOREIGN PATENT DOCUMENTS

| | | |
|---|---|---|
| CN | 1420128 | 5/2003 |
| CN | 101165068 | 4/2008 |
| WO | WO03/087131 | 10/2003 |
| WO | WO2009/123894 | 10/2009 |

OTHER PUBLICATIONS

Strome et al., The Oncologist, 2007; 12:1084-95.*
Brand et al., Anticancer Res. 2006; 26:463-70.*

* cited by examiner

*Primary Examiner* — Sheela J Huff
(74) *Attorney, Agent, or Firm* — Cesari and McKenna, LLP

(57) ABSTRACT

The invention provides a fully human anti-HER2 monoclonal antibody, which has an amino acid sequence of heavy chain variable region as shown in SEQ ID NO: 6 and an amino acid sequence of light chain variable region as shown in SEQ ID NO: 8. The invention also discloses the nucleotide sequence encoding the antibody, the expression vector and the host cell comprising the nucleotide sequence, and the use of the antibody for manufacturing the medicament for the treatment of tumor.

17 Claims, 3 Drawing Sheets

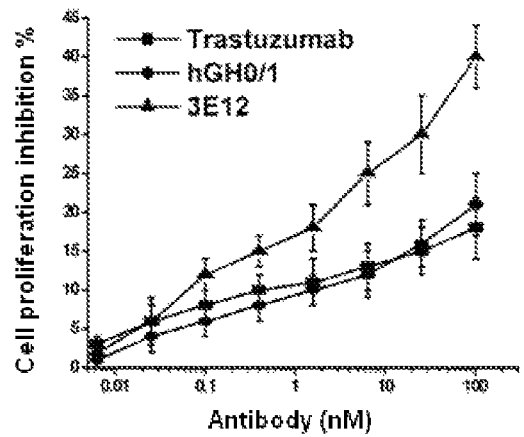
Fig. 2-1
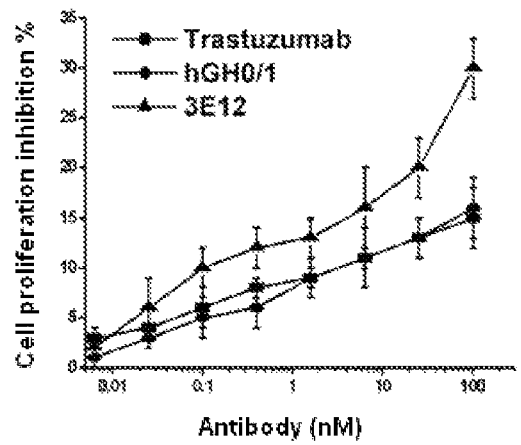
Fig. 2-2
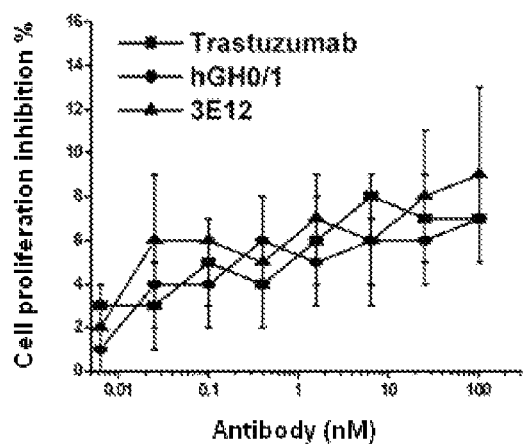
Fig. 2-3
Fig. 2

SEQUENCE LISTING

```
<160> NUMBER OF SEQ ID NOS: 12

<210> SEQ ID NO 1
<211> LENGTH: 990
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of human antibody heavy
      chain constant region (CH)

<400> SEQUENCE: 1
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
```

```
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggaaga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccggtaaa                                      990
```

<210> SEQ ID NO 2
<211> LENGTH: 330
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of human antibody heavy
      chain constant region (CH)

<400> SEQUENCE: 2

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

195                 200                 205
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 318
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of human antibody light
      chain constant region (CL)

<400> SEQUENCE: 3
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgcccteca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgt                                                   318

<210> SEQ ID NO 4
<211> LENGTH: 106
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of human antibody light
      chain constant region (CL)

<400> SEQUENCE: 4

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys

```
                65                  70                  75                  80
His Lys Val Tyr Ala Cys Glu Val Thr His Gln Gly Leu Ser Ser Pro
                        85                  90                  95

Val Thr Lys Ser Phe Asn Arg Gly Glu Cys
                    100                 105

<210> SEQ ID NO 5
<211> LENGTH: 366
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of heavy chain variable
      region of fully human antibody 3E12

<400> SEQUENCE: 5
gaggtgcatc tggtggagtc tgggggaggc ttggtacagc ctggggggc cctgagactc      60 tcctgtgcag cctctggatt caccttcagt aactacgaca tgcactgggt ccgccaagct    120
acaggaaaag gtctggagtg ggtctcagcc aatggtactg ctggtgacac atactatcca    180
ggctccgtga aggggcgatt caccatctcc agagaaaatg ccaagaactc cttgtatctc    240
caaatgaaca gcctgagagc cggggacacg gctgtgtatt actgtgcaag agacgtggat    300
atagtggcta cgattacgga ctactttgac tactggggcc aaggaaccct ggtcaccgtc    360
tcctca                                                               366

<210> SEQ ID NO 6
<211> LENGTH: 122
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of heavy chain variable
      region of fully human antibody 3E12

<400> SEQUENCE: 6

Glu Val His Leu Val Glu Ser Gly Gly Gly Leu Val Gln Pro Gly Gly
1               5                   10                  15

Ala Leu Arg Leu Ser Cys Ala Ala Ser Gly Phe Thr Phe Ser Asn Tyr
            20                  25                  30

Asp Met His Trp Val Arg Gln Ala Thr Gly Lys Gly Leu Glu Trp Val
        35                  40                  45

Ser Ala Asn Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Val Asp Ile Val Ala Thr Ile Thr Asp Tyr Phe Asp Tyr Trp
            100                 105                 110

Gly Gln Gly Thr Leu Val Thr Val Ser Ser
        115                 120

<210> SEQ ID NO 7
<211> LENGTH: 345
<212> TYPE: DNA
<213> ORGANISM: Artificial sequence
```

<220> FEATURE:
<223> OTHER INFORMATION: Synthetic oligonucleotide
<220> FEATURE:
<221> NAME/KEY: misc_feature
<223> OTHER INFORMATION: Nucleotide sequence of light chain variable
      region of fully human antibody 3E12

<400> SEQUENCE: 7

```
gatattgtga tgacccagac tccactctcc tcacctgtca cccttggaca gccggcctcc    60
atctcctgca ggtctagtca aagcctcgta cacagtgatg gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcggggtt tattactgca tgcaagctac acaatttcct   300
caccagtgga cgttcggcca agggaccaag gtggaaatca aacgt                    345
```

<210> SEQ ID NO 8
<211> LENGTH: 115
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of light chain variable
      region of fully human antibody 3E12

<400> SEQUENCE: 8

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro His Gln Trp Thr Phe Gly Gly Gly Thr Lys Val Glu
            100                 105                 110

Ile Lys Arg
        115
```

<210> SEQ ID NO 9
<211> LENGTH: 1356
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of heavy chain of fully
      human antibody 3E12

<400> SEQUENCE: 9

```
gaggtgcatc tggtggagtc tgggggaggc ttggtacagc ctggggggtc cctgagactc    60
tcctgtgcag cctctggatt caccttcagt aactacgaca tgcactgggt ccgccaagct   120
acaggaaaag gtctggagtg ggtctcagcc aatggtactg ctggtgacac atactatcca   180
```

```
ggctccgtga agggcgatt caccatctcc agagaaaatg ccaagaactc cttgtatctt      240
caaatgaaca gcctgagagc cggggacacg gctgtgtatt actgtgcaag agacgtggat      300
atagtggcta cgattacgga ctactttgac tactggggcc aaggaaccct ggtcaccgtc      360
tcctcagcta gcaccaaggg cccatcggtc ttccccctgg cacctcctc caagagcacc       420 tctgggggca gcggccct gggctgcctg gtcaaggact acttccccga accggtgacg        480
gtgtcgtgga actcaggcgc cctgaccagc ggcgtgcaca ccttcccggc tgtcctacag      540
tcctcaggac tctactccct cagcagcgtg gtgaccgtgc cctccagcag cttgggcacc      600
cagacctaca tctgcaacgt gaatcacaag cccagcaaca ccaaggtgga caagagagtt      660
gagcccaaat cttgtgacaa aactcacaca tgcccaccgt gcccagcacc tgaactcctg      720
gggggaccgt cagtcttcct cttccccca aaacccaagg acaccctcat gatctcccgg       780 accctgagg tcacatgcgt ggtggtggac gtgagccacg aagaccctga ggtcaagttc       840
aactggtacg tggacggcgt ggaggtgcat aatgccaaga caaagccgcg ggaggagcag      900
tacaacagca cgtaccgtgt ggtcagcgtc ctcaccgtcc tgcaccagga ctggctgaat      960
ggcaaggagt acaagtgcaa ggtctccaac aaagccctcc cagcccccat cgagaaaacc     1020
atctccaaag ccaaagggca gccccgagaa ccacaggtgt acaccctgcc cccatcccgg     1080
gaggagatga ccaagaacca ggtcagcctg acctgcctgg tcaaaggctt ctatcccagc     1140
gacatcgccg tggagtggga gagcaatggg cagccggaga caactacaa gaccacgcct     1200 cccgtgctgg actccgacgg ctccttcttc ctctatagca agctcaccgt ggacaagagc     1260
aggtggcagc aggggaacgt cttctcatgc tccgtgatgc atgaggctct gcacaaccac     1320
tacacgcaga agagcctctc cctgtccccg ggtaaa                               1356
```

<210> SEQ ID NO 10
<211> LENGTH: 452
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of heavy chain of fully
      human antibody 3E12

<400> SEQUENCE: 10

```
Glu Val His Leu Val Glu Ser Gly Gly Gly Leu Val Gln Pro Gly Gly
1               5                   10                  15

Ala Leu Arg Leu Ser Cys Ala Ala Ser Gly Phe Thr Phe Ser Asn Tyr
            20                  25                  30

Asp Met His Trp Val Arg Gln Ala Thr Gly Lys Gly Leu Glu Trp Val
        35                  40                  45

Ser Ala Asn Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Val Asp Ile Val Ala Thr Ile Thr Asp Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
```

```
                  130                135                140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 11
<211> LENGTH: 663
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of light chain of fully
      human antibody 3E12

<400> SEQUENCE: 11
gatattgtga tgacccagac tccactctcc tcacctgtca cccttggaca gccggcctcc    60
atctcctgca ggtctagtca aagcctcgta cacagtgatg gaaacaccta cttgagttgg   120
```

```
cttcagcaga ggccaggcca gcctccaaga ctcctaattt ataagatttc taaccggttc    180 tctgggtcc cagacagatt cagtggcagt ggggcaggga cagatttcac actgaaaatc    240
agcagggtgg aagctgagga tgtcggggtt tattactgca tgcaagctac acaatttcct    300
caccagtgga cgttcggcca agggaccaag gtggaaatca aacgtactgt ggctgcacca    360
tctgtcttca tcttcccgcc atctgatgag cagttgaaat ctggaactgc ctctgttgtg    420
tgcctgctga ataacttcta tcccagagag gccaaagtac agtggaaggt ggataacgcc    480
ctccaatcgg gtaactccca ggagagtgtc acagagcagg acagcaagga cagcacctac    540
agcctcagca gcaccctgac gctgagcaaa gcagactacg agaaacacaa agtctacgcc    600
tgcgaagtca cccatcaggg cctgagctcg cccgtcacaa agagcttcaa caggggagag    660
tgt                                                                  663
```

```
<210> SEQ ID NO 12
<211> LENGTH: 221
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of light chain of fully
      human antibody 3E12

<400> SEQUENCE: 12

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro His Gln Trp Thr Phe Gly Gln Gly Thr Lys Val Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220
```

FULLY HUMANIZED ANTI-HER2 ANTIBODY, PREPARATION METHOD AND USE THEREOF

CROSS-REFERENCE TO RELATED APPLICATIONS

This application is the National Stage of International Application No. PCT/CN2010/000511, filed on Apr. 16, 2010, which claims the priority of Chinese Application No. 201010125241.0, filed on Feb. 25, 2010. The contents of both applications are hereby incorporated by reference in their entirety.

FIELD OF THE INVENTION

The present invention relates to the field of biotechnology. In particular, the present invention relates to a fully human monoclonal antibody, the preparation method and use thereof.

BACKGROUND OF THE INVENTION

Breast cancer is one of the most common malignant tumors in women. More than one million new cases of breast cancer occur worldwide annually, and nearly 400 thousand people died from breast cancer every year. In recent years, the incidence of breast cancer showed a clear upward trend in the world. Despite in high and low endemic areas, the incidence of breast cancer increases by 5-20%. The growth trend of the incidence of breast cancer in Asian women has been significantly higher than that in the United States and Europe. In China, breast cancer has become the primary malignant tumor in women in some cities. The common treatments for breast cancer include surgery, chemicotherapy and endocrine therapy and so on. Although these conventional treatments may prolong survival in patients to a large extent, their side effects are serious and their therapeutic effect is hard to be further improved. Targeted cancer therapy is a new treatment for cancer that has arisen in recent years, of which the representative is antitumor monoclonal antibody.

HER2 (human epidermal growth factor receptor 2) is a transmembrane protein with tyrosine kinase activity, having a molecular weight of about 185 KD. Anti-HER2 humanized monoclonal antibody may specifically bind to HER2, and has antitumor mechanisms as follows: specifically binding to the extracellular domain of HER2 receptor to block the constitutive activation of HER2 homodimers and interfere the heterodimer formation of HER2 with other ErbB family members; mediating the endocytosis and the degradation in lysosomes of HER2 receptor; activating PTEN (phosphatase and tensin homology) and blocking PI3K (Phosphatidylinositol 3-kinase) signal channel; inhibiting tumor cell proliferation by regulation of cell cycle; promoting tumor cell apoptosis; inhibiting tumor angiogenesis; ADCC (antibody-dependent cell-mediated cytotoxicity) effect; inhibiting DNA repair; increasing the cytotoxicity of chemotherapeutic agents; reversing the resistance of tumor cells to the killing effects of host cell factors, and etc. (Pergram M, Ngo D, Application and potential limitations of animal models utilized in the development of trastuzumab (Herceptin®): A case study. Adv Drug Deliv Rev. 2006; 58:723-34).

Anti-HER2 humanized monoclonal antibody (Trastuzumab, trade name: Herceptin) has been used in clinical trials to treat patients with HER2 overexpressing metastatic breast cancer as single drug, who had received but failed one or more chemotherapy regimens for their metastases. This drug may be used in combination with paclitaxel or anthracyclines (doxorubicin or epirubicin) plus cyclophosphamide in clinical trials as first-line drugs to treat HER2 overexpressing metastatic breast cancer (Merlin J L, Barberi-Heyob M, Bachmann N, In vitro comparative evaluation of trastuzumab (Herceptin) combined with paclitaxel (Taxol) or docetaxel (Taxotere) in HER2-expressing human breast cancer cell lines. Ann Oncol. 2002; 13:1743-8). But Trastuzumab is a humanized antibody that maintains the murine CDR regions and a small amount of murine FR residues, which still has not been fully humanized and the affinity is not high.

SUMMARY OF THE INVENTION

The present invention constructs a very large human natural phage antibody library and obtains a fully human anti-HER2 antibody 3E12 by selecting therefrom.

More particularly, the present invention provides a fully human anti-HER2 antibody, having an amino acid sequence of heavy chain variable region as shown in SEQ ID NO: 6, and an amino acid sequence of light chain variable region as shown in SEQ ID NO: 8.

The above fully human anti-HER2 antibody according to the present invention has an amino acid sequence of heavy chain as shown in SEQ ID NO: 10, and an amino acid sequence of light chain as shown in SEQ ID NO: 12.

The present invention also provides an isolated nucleotide encoding the above fully human anti-HER2 antibody.

The above nucleotide according to the present invention has a nucleotide sequence encoding heavy chain variable region of the fully human anti-HER2 antibody as shown in SEQ ID NO: 5, and a nucleotide sequence encoding light chain variable region of the fully human anti-HER2 antibody as shown in SEQ ID NO: 7.

The above nucleotide according to the present invention has a nucleotide sequence encoding heavy chain of the fully human anti-HER2 antibody as shown in SEQ ID NO: 9, and a nucleotide sequence encoding light chain of the fully human anti-HER2 antibody as shown in SEQ ID NO: 11.

The present invention also provides an expression vector containing the above nucleotide, which is pcDNA3.1/ZEO(+) or pcDNA3.1 (+).

The present invention also provides a host cell transfected with the above expression vector, which is a CHO-K1 cell.

The present invention further provides a method for preparing the above fully human antibody, comprising selecting human phage antibody library to obtain a fully human anti-HER2 single-chain antibody with high affinity; constructing an eukaryotic expression vector of the complete molecular of the fully human anti-HER2 antibody; expressing the complete molecular of fully human anti-HER2 antibody in CHO cells; and purifying the complete molecular of the fully human anti-HER2 antibody.

The present invention also provides a use of the above fully human antibody in preparing medicines for treatment of tumor. The tumor is a Her2-overexpressing tumor, and more particularly is breast cancer.

The obtained antibody are used to perform a series of experiments in the present invention and the experiment results show that compared to humanized antibody Trastuzumab (rhumAb 4D5), and humanized antibody hGH0/1 disclosed in Chinese Patent Application No. 01132225.X entitled "Humanized Anti-HER2 Monoclonal Antibody, Preparation Method and Pharmaceutical Composition Thereof" filed on Nov. 16, 2001, 3E12 has higher antibody affinity and stronger inhibition effect on the cell proliferation of Her2-overexpressing breast cancer cells, and apoptosis-

BRIEF DESCRIPTION OF DRAWINGS

FIG. 1 shows the results of the apoptosis experiment of anti-HER2 antibody, wherein FIG. 1-1: SK-BR3 cell; FIG. 1-2: BT-474 cell; FIG. 1-3: MCF-7 cell);

FIG. 2 shows the results of the growth inhibition experiment of anti-HER2 antibody, wherein FIG. 2-1: SK-BR3 cell; FIG. 2-2: BT-474 cell; FIG. 2-3: MCF-7 cell);

FIG. 3 shows the results of the in vivo antitumor experiment of anti-HER2 antibody.

DETAILED DESCRIPTION OF THE INVENTION

Figure 1:
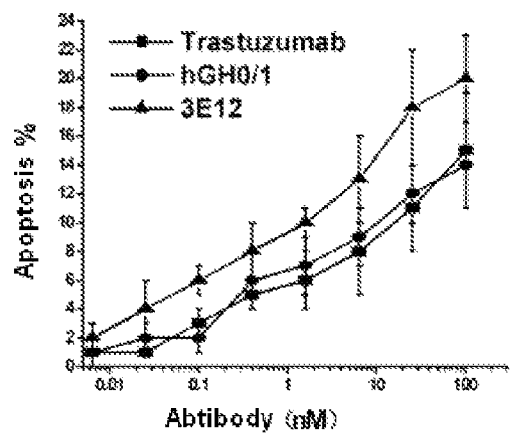
Figure 1:
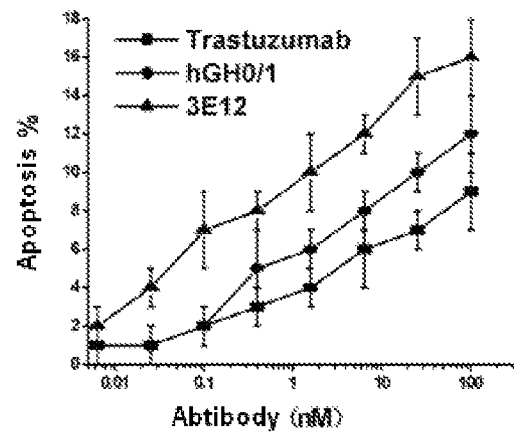
Figure 1:
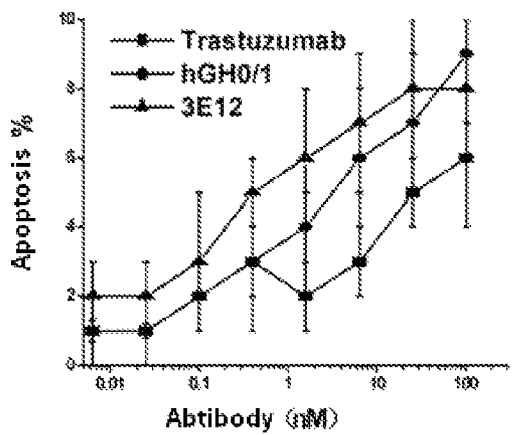

The following examples and experiment examples are used to further illustrate the present invention only and should not be construed to limit the present invention.

Example

Preparation of Antibody (1) Cloning of Genes Encoding Human Antibody Light and Heavy Chain Constant Region Healthy human peripheral blood lymphocytes were isolated with lymphocyte separation medium (Dingguo Biotechnology Development Company, China) and total RNA was extracted using Trizol reagent (Invitrogen). The genes encoding antibody heavy and light chain constant regions were amplified by RT-PCR reaction, with the primers designed according to the sequences reported in the reference (Cell, 1980, 22: 197-207) and reference (Nucleic Acids Research, 1982, 10: 4071-4079), respectively. The PCR products were purified by agarose gel electrophoresis and recovered and cloned into pGEM-T vectors (Promega). Correct clones were obtained by sequencing verification. SEQ ID NO: 1 and SEQ ID NO: 2 showed the nucleotide sequence and amino acid sequence of the heavy chain constant region ($C_H$), respectively. SEQ ID NO: 3 and SEQ ID NO: 4 showed the nucleotide sequence and amino acid sequence of the light chain constant region ($C_L$), respectively. In this example, the correct clones were designated as pGEM-T/$C_H$ and pGEM-T/$C_L$.

(2) Preparation of cDNA 20 ml of peripheral blood was collected from each of 50 healthy people and mononuclearcells were isolated with lymphocyte separation medium (Tianjin blood research Institute of Medical Science). Total cellular RNA was extracted from the isolated human peripheral blood lymphocytes using Trizol reagent (Invitrogen). cDNA was reverse transcribed using cDNA reverse transcription kit (Shanghai Biocolor Biotechnolgy Ltd.). The above procedures were performed according to the manufacturer's instructions.

(3) Design of Primers $V_H$Back, $V_H$For, $V_L$Back and $V_L$For, the primers for cloning genes of human antibody heavy chain variable region ($V_H$) and light chain variable region ($V_L$), were designed and synthesized according to the reference (Immunotechnology, 1998, 3:271-278). Sequences of $V_H$Back, $V_H$For, $V_L$Back and $V_L$For were shown in Immunotechnology, 1998, 3:271-278. Wherein, $V_H$Back primer was added with an Sfi I site-containing sequence: atg gcc cag ccg gcc atg gcc at the 5' end; $V_H$For primer was added with a sequence: gcc aga acc acc gcc gcc gga gcc acc acc gcc at the 5' end; $V_L$Back primer was added with a sequence: tcc ggc ggc ggt ggt tct ggc gga ggc gga tct at the 5' end; and $V_L$For primer was added with a Not I site-containing sequence: atg cgg ccg c at the 5' end.

(4) Construction and Selection of Phage Antibody Library

Phage single-chain antibody library was constructed with the cDNA of (2) and the primers of (3) using recombinant Phage antibody system kit (Amersham Biosciences) and then selected with a specific antigen. The methods of constructing and selecting the antibody library were performed according to the instructions of recombinant Phage antibody system kit. The specific antigen "human HER2 extracellular protein" used for selection was prepared according to the method disclosed in the reference (Proc Natl Acad Sci USA, 1992, 89: 4285-4289). A human anti-HER2 single-chain antibody 3E12ScFv was obtained after several times of selection, and its gene sequence was obtained by sequencing. SEQ ID NO: 5 and SEQ ID NO: 6 show the nucleotide sequence and amino acid sequence of the heavy chain variable region ($V_H$) of 3E12ScFv, respectively. SEQ ID NO: 7 and SEQ ID NO: 8 show the nucleotide sequence and amino acid sequence of the light chain variable region ($V_L$) of 3E12ScFv, respectively.

(5) Expression of Fully Human Antibody in Eukaryotic Cells

3E12ScFv genes and pGEM-T/$C_H$ vectors were used as template to synthesize fully human antibody heavy chain genes by overlapping PCR. The reaction conditions were: 95° C. for 15 min; 94° C. for 50 sec, 58° C. for 50 sec, 72° C. for 50 sec, for 30 cycles; 72° C. for 10 min. Besides, the fully human antibody heavy chain genes were allowed to contain HindIII restriction enzyme sites and a signal peptide gene sequence at the 5' end and contain translation stop codens TAA and EcoRI restriction enzyme sites at the 3' end. The sequence of the signal peptide was: (ATGGATTTTCAGGTGCAGATTTTCAGCTTCCTGCTAATCAGTGC-CTCAGTCATAAT ATCCAGAGGA). Finally, PCR amplification products were separated by agarose gel electrophoresis and the band of interest was recovered and cloned into pGEM-T vectors (Promega) to select and sequence positive clones. Clones with the correct sequence were selected and digested with Hind III and EcoRI, and the fully human antibody heavy chain fragments 3E12$V_H C_H$ were purified and recovered by agarose gel electrophoresis and ligated into the HindIII and EcoRI-digested plasmids pcDNA3.1(+) (Invitrogen) to construct fully human heavy chain eukaryotic expression vectors pcDNA3.1(+) (3E12$V_H C_H$).

3E12ScFv genes and pGEM-T/$C_L$ vectors were used as template to synthesize fully human antibody light chain genes by overlapping PCR. The reaction conditions were: 95° C. for 15 min; 94° C. for 50 sec, 58° C. for 50 sec, 72° C. for 50 sec, for 30 cycles; 72° C. for 10 min. The obtained PCR products contained HindIII restriction enzyme sites and a signal peptide gene sequence at the 5' end and contained translation stop codens TAA and EcoRI restriction enzyme sites at the 3' end. The sequence of the signal peptide was: (ATGGATTTTCAG-GTGCAGATTTTCAGCTTCCTGCTAAT-CAGTGCCTCAGTCATAAT ATCCAGAGGA). Clones with the correct sequences were selected and digested with Hind III and EcoRI, and the fully human antibody light chain fragments 3E12$V_L C_L$ were purified and recovered by agarose gel electrophoresis and ligated into the HindIII and EcoRI-digested plasmids pcDNA3.1/ZEO(+) (Invitrogen) to construct fully human light chain eukaryotic expression vectors pcDNA3.1/ZEO(+) (3E12$V_L C_L$).

$3 \times 10^5$ CHO-K1 cells (ATCC CRL-9618) were inoculated into 3.5 cm tissue culture dishes, and transfected when the cells were cultured to 90-95% confluence: 10 μg of plasmids (4 μg of plasmids pcDNA3.1(+) (3E12$V_H C_H$), bug of plasmids pcDNA3.1/ZEO(+) (3E12$V_L C_L$)) and 20 μl of Lipofectamine2000 Reagent (Invitrogen) were taken to perform transfection according to the instructions of Lipofectamine2000 Reagent kit. After transfection for 24 hours, the cells were transferred to DMEM medium containing 600 μg/ml G418 (Invitrogen) and 250 μg/ml Zeocin (Invitrogen) to select resistant clones. Cell culture supernatants were taken to select high-expressing clones by ELISA: ELISA plates were coated with goat anti-human IgG (Fc) (KPL) overnight at 4° C. and blocked with 2% BSA-PBS at 37° C. for 2 h; the culture supernatants of resistant clones to be tested or standard sample (Human myeloma IgG1, κ) (Sigma) were added and warm incubated at 37° C. for 2 h; HRP-goat anti-human IgG (κ) (Southern Biotechnology Associates) was added and warm incubated at 37° C. for 1 h for combining reaction, and chromogenic reagent TMB was added and reacted at 37° C. for 5 min, finally $H_2SO_4$ was used to stop the reaction and $A_{450}$ value was measured. The high-expressing clones obtained by selection were enlarged cultured in serum-free medium, and fully human antibodies 3E12 were isolated and purified by Protein A affinity column (GE). The purified antibodies were dialyzed against PBS and finally quantified by UV absorbance. SEQ ID NO: 9 and SEQ ID NO: 10 show the nucleotide sequence and amino acid sequence of the heavy chain of fully human antibody 3E12, respectively. SEQ ID NO: 11 and SEQ ID NO: 12 show the nucleotide sequence and amino acid sequence of the light chain of fully human antibody 3E12, respectively.

Experimental Examples hGH0/1 was prepared according to the method described in Chinese Patent Application No. 01132225.X entitled "Humanized Anti-HER2 Monoclonal Antibody, Preparation Method and Pharmaceutical Composition Thereof" filed on Nov. 16, 2001.

Apoptosis Experiment of Anti-HER2 Antibody

Human breast cancer cells SK-BR-3 (high HER2-expressing, ATCC: HTB-30), BT-474 (medium HER2-expressing, ATCC: HTB-20) and MCF-7 (low HER2-expressing, ATCC: HTB-22) were cultured with different dilution degrees of anti-HER2 antibodies (including Trastuzumab, hGH0/1, 3E12) at 37° C. for 20 h, respectively. After washing the cells, the percentage of early apoptotic cells was detected according to the instructions of AnnexinV/PI kit (BD). The results of anti-apoptotic experiment are shown in FIG. 1. The cell-killing ability of 3E12 antibody was significantly stronger than that of Trastuzumab antibody and hGH0/1 (when the antibody concentration was ≥0.025 nM), $P<0.05$, t test), and the same results were also be demonstrated in BT-474 cells (when the antibody concentration was ≥0.025 nM, $P<0.05$, t test). However, in low HER2 expressing MCF-7 cells, the killing ability of 3E12 antibody was close to that of Trastuzumab antibody and GH0/1 antibody. These results exhibited that 3E12 antibody had HER2 specificity in killing cells, and had a stronger ability to kill medium and high HER2 expressing cells than Trastuzumab antibody and hGH0/1 antibody.

Cell Growth Inhibition Experiment of Anti HER2 Antibody

Human breast cancer cells SK-BR-3, BT-474 and MCF-7 cells were incubated with different dilution degrees of anti-HER2 antibodies at 37° C., respectively. On the fifth day, the growth inhibition ratio was calculated after reading by MTT staining. The results of growth inhibition experiment are shown in FIG. 2. The ability of 3E12 antibody to inhibit SK-BR3 cell growth was significantly stronger than that of Trastuzumab antibody and hGH0/1 (when the antibody concentration was ≥0.1 nM, $P<0.05$, t test), and the same results were also be demonstrated in BT-474 cells (when the antibody concentration was ≥0.1 nM), $P<0.05$, t test). However, in low HER2 expressing MCF-7 cells, the cell inhibiting ability of 3E12 antibody was close to that of Trastuzumab antibody and GH0/1 antibody. These results exhibited that 3E12 antibody had HER2 specificity in inhibiting cell growth, and had a stronger ability to inhibit medium and high HER2 expressing cells than Trastuzumab antibody and hGH0/1 antibody.

In Vivo Antitumor Experiments of Anti HER2 Antibody

Figure 3:
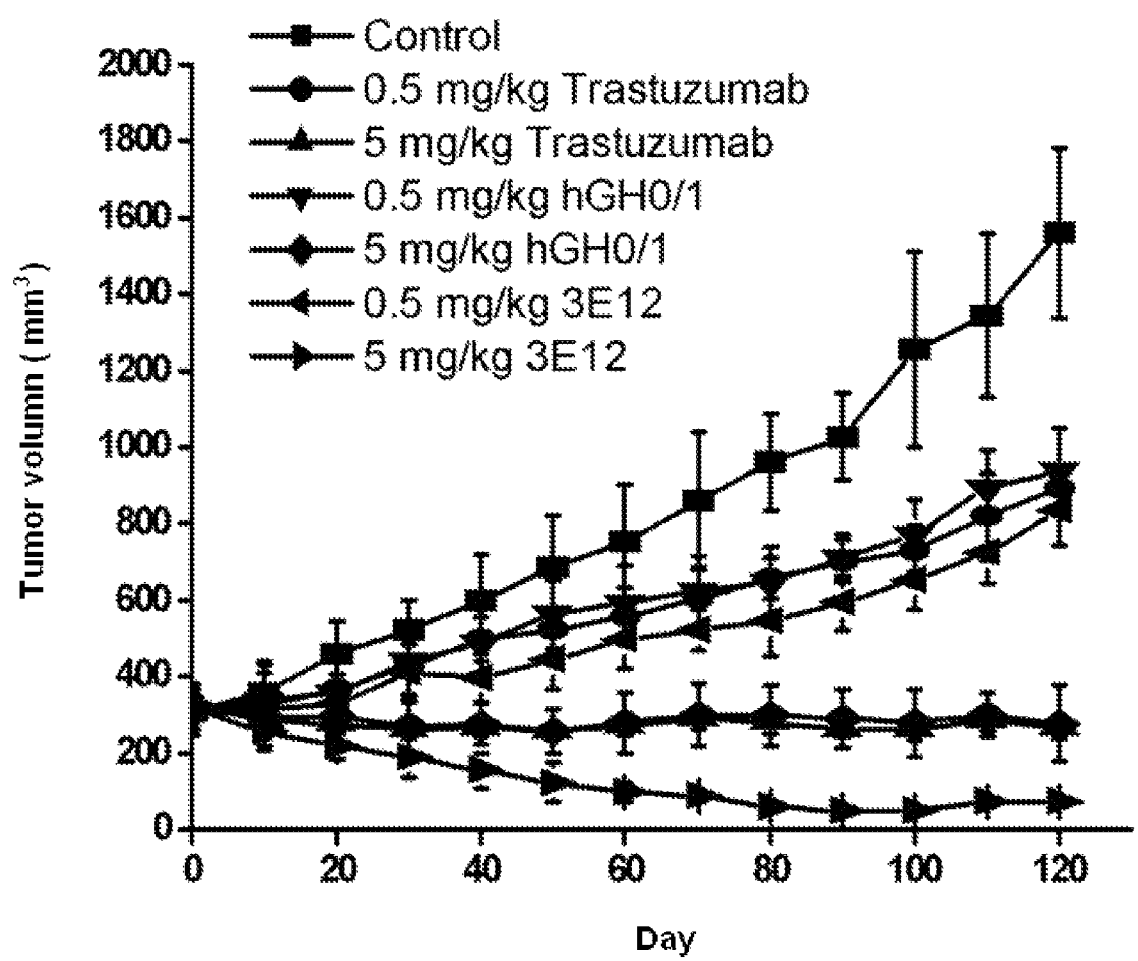

Each of SCID mice (purchased from Slack, Shanghai) was subcutaneously inoculated with high HER2 expressing human breast cancer cells BT-747 on $0^{th}$ day, and when the tumor grew to 0.3 $cm^3$, the tumor-bearing mice were intraperitoneally injected with various anti-HER2 antibodies at 0.5, 5 mg/kg for twice a week and continuously treated for 3 weeks. The changes of body weight of mice and tumor size were regularly observed for a total of 120 days. The antitumor treatment effect of anti-HER2 antibodies was evaluated. The results of antitumor experiment in vivo are shown in FIG. 3. The ability of 3E12 antibody to inhibit the growth of high HER2 expressing breast cancer cells BT-747 was significantly stronger than that of Trastuzumab antibody and hGH0/1 (at the dose of 25 mg/kg, on the $50^{th}$, $60^{th}$, $70^{th}$, $80^{th}$, $90^{th}$, $100^{th}$, $110^{th}$, 120th day, $P<0.05$, Mann-Whitney test).

What is claimed is:

1. A fully human anti-HER2 antibody, having a heavy chain variable region amino acid sequence as shown in SEQ ID NO: 6 and a light chain variable region amino acid sequence as shown in SEQ ID NO: 8.

2. The fully human anti-HER2 antibody of claim 1, having a heavy chain amino acid sequence as shown in SEQ ID NO: 10 and a light chain amino acid sequence as shown in SEQ ID NO: 12.

3. An isolated nucleic acid encoding the fully human anti-HER2 antibody of claim 1.

4. The nucleic acid of claim 3, having a nucleotide sequence encoding heavy chain variable region of the fully human anti-HER2 antibody as shown in SEQ ID NO: 5 and a nucleotide sequence encoding light chain variable region of the fully human anti-HER2 antibody as shown in SEQ ID NO: 7.

5. The nucleic acid of claim 4, having a nucleotide sequence encoding heavy chain of the fully human anti-HER2 antibody as shown in SEQ ID NO: 9 and a nucleotide sequence encoding light chain of the fully human anti-HER2 antibody as shown in SEQ ID NO: 11.

6. An expression vector containing the nucleic acid of claim 3, the vector being pcDNA3.1/ZEO(+) or pcDNA3.1(+).

7. A host cell transfected with the expression vector of claim 6, the host cell being a CHO-K1 cell.

8. An isolated nucleic acid encoding the fully human anti-HER2 antibody of claim 2.

9. The nucleic acid of claim 8, having a nucleotide sequence encoding heavy chain variable region of the fully human anti-HER2 antibody as shown in SEQ ID NO: 5 and a nucleotide sequence encoding light chain variable region of the fully human anti-HER2 antibody as shown in SEQ ID NO: 7.

10. The nucleic acid of claim 4, having a nucleotide sequence encoding heavy chain of the fully human anti-HER2 antibody as shown in SEQ ID NO: 9 and a nucleotide sequence encoding light chain of the fully human anti-HER2 antibody as shown in SEQ ID NO: 11.

11. An expression vector containing the nucleic acid of claim 4, the vector being pcDNA3.1/ZEO(+) or pcDNA3.1(+).

12. An expression vector containing the nucleic acid of claim 5, the vector being pcDNA3.1/ZEO(+) or pcDNA3.1(+).

13. An expression vector containing the nucleic acid of claim 8, the vector being pcDNA3.1/ZEO(+) or pcDNA3.1(+).

14. An expression vector containing the nucleic acid of claim 9, the vector being pcDNA3.1/ZEO(+) or pcDNA3.1(+).

15. An expression vector containing the nucleic acid of claim 10, the vector being pcDNA3.1/ZEO(+) or pcDNA3.1(+).

16. A method of treating breast cancer in a subject, comprising administering to a subject in need thereof the fully human anti-HER2 antibody of claim 1.

17. The method of claim 16, wherein the antibody has a heavy chain amino acid sequence as shown in SEQ ID NO: 10 and a light chain amino acid sequence sequence as shown in SEQ ID NO: 12.

* * * * *